US00PP32207P2

(12) United States Plant Patent
Van Swieten

(10) Patent No.: US PP32,207 P2
(45) Date of Patent: Sep. 15, 2020

(54) ***PHALAENOPSIS* ORCHID PLANT NAMED 'PHALGUIQDI'**

(50) Latin Name: ***Phalaenopsis* hybrid**
Varietal Denomination: PHALGUIQDI

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/602,848

(22) Filed: Dec. 11, 2019

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
See application file for complete search history.

*Primary Examiner* — Annette H Para
(74) *Attorney, Agent, or Firm* — Jondle & Associates, P.C.

(57) ABSTRACT

A new and distinct variety of *Phalaenopsis* plant named 'PHALGUIQDI', particularly characterized by having purplish-pink striped flowers with red-purple lips, peduncles that are long and sturdy, and is propagated by meristem tissue culture, is disclosed.

3 Drawing Sheets

Genus and species: *Phalaenopsis* hybrid.
Variety denomination: 'PHALGUIQDI'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGUIQDI'.

The new *Phalaenopsis* plant is a product of a planned breeding program conducted by the inventor in Bleiswijk, the Netherlands. The objective of this breeding program was to create a new *Phalaenopsis* plant with numerous attractive purplish-pink striped flowers with red-purple lips, suitable for potted plant production.

The new *Phalaenopsis* plant 'PHALGUIQDI' is a result of cross-pollination made by the inventor in July 2009 in Bleiswijk, the Netherlands, of the proprietary female, or seed parent, *Phalaenopsis* hybrid '23426-01' (unpatented) with the proprietary male, or pollen parent, *Phalaenopsis* hybrid '14261-01' (unpatented).

The new *Phalaenopsis* was selected by the inventor as a single plant within the progeny of the stated cross-pollination in a controlled greenhouse in Bleiswijk, the Netherlands, in July 2012. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 16, 2019, by Applicant who obtained the subject matter disclosed directly from the inventor. 'PHALGUIQDI' has not been made publicly available or sold anywhere in the world prior to the effective filing date of this application with the exception of sales or disclosures made one year or less before the effective filing date of this claimed invention by Applicant who obtained 'PHALGUIQDI' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALGUIQDI' as a new and distinct variety of *Phalaenopsis* plant:

1) Purplish-pink striped flowers;
2) Red-purple lips; and
3) Peduncle is long and sturdy.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in October 2019. Colors in the photographs may differ from the color values cited in the detailed botanical description, which accurately describe the actual colors of the new variety.

DESCRIPTION OF THE NEW VARIETY

Figure 1:
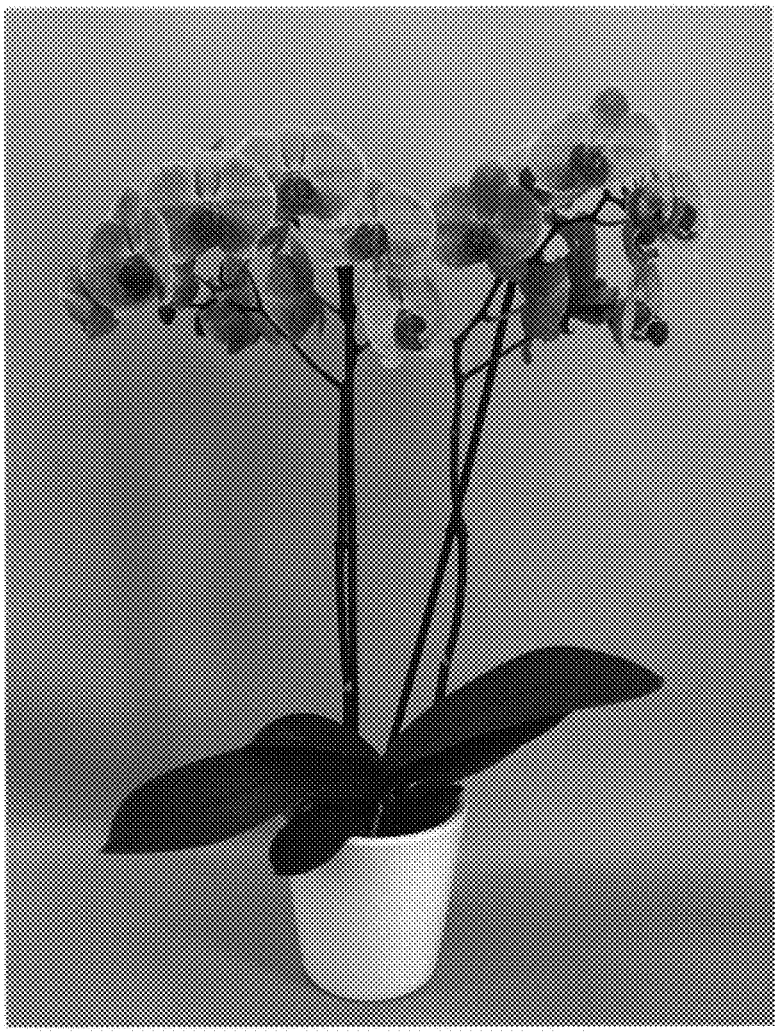
FIG. 1 shows the overall plant habit, including blooms, buds, and foliage of 'PHALGUIQDI'.
Figure 2:
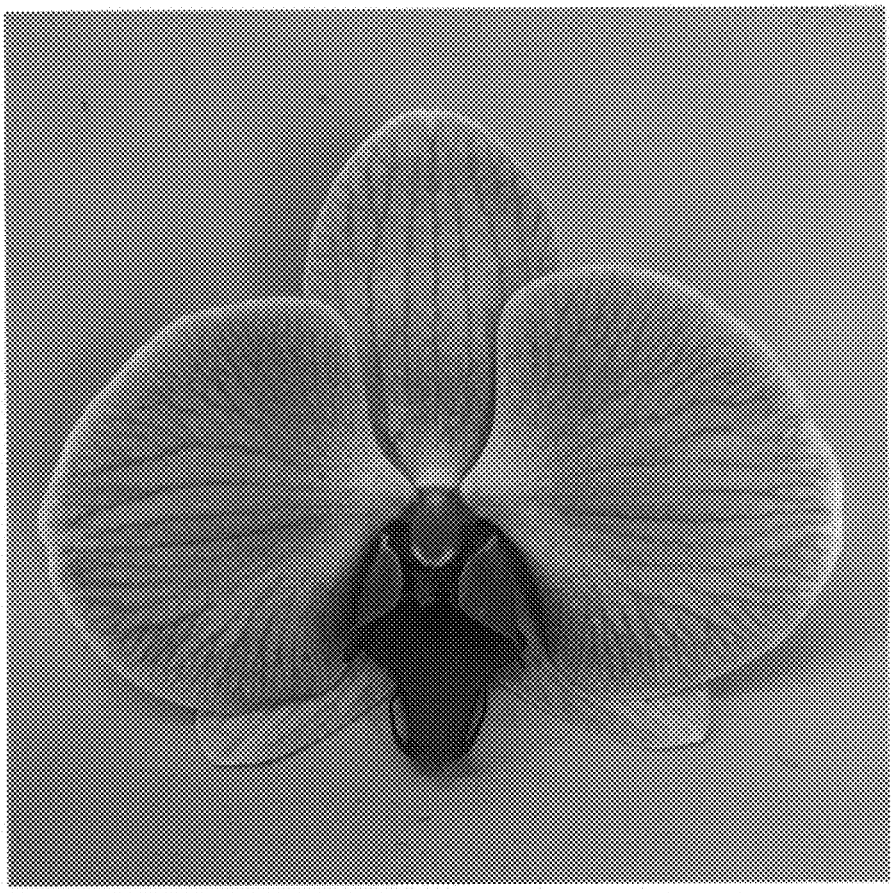
FIG. 2 shows a close-up of a flower of 'PHALGUIQDI'.
Figure 3:
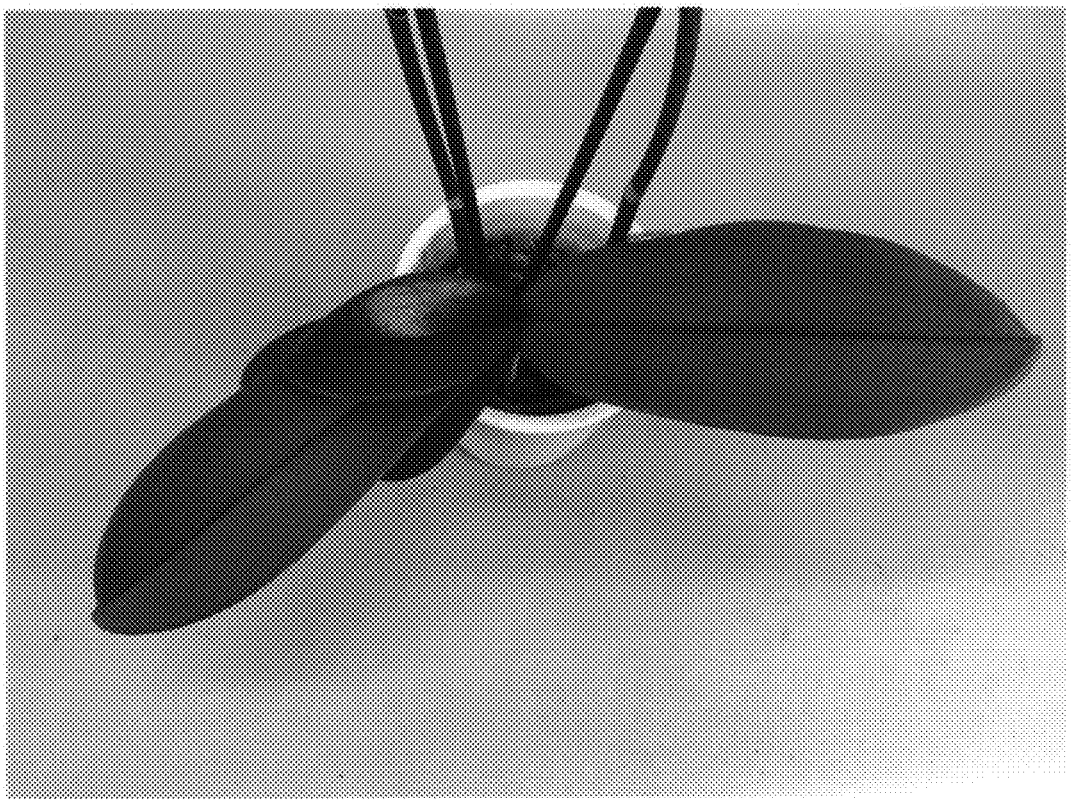
FIG. 3 shows an overhead view of the leaves of 'PHALGUIQDI'.

The following detailed description sets forth the distinctive characteristics of 'PHALGUIQDI'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in October 2019 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGUIQDI'.

Parentage:

*Female parent*.—*Phalaenopsis* cultivar '23426-01' (unpatented).

*Male parent*.—*Phalaenopsis* cultivar '14261-01' (unpatented).

Propagation:

*Type*.—Meristem tissue culture.

Roots:

*Root description*.—Greyed-green (between RHS 190B and 190C) colored roots with branching lateral roots having yellow-green (RHS 146D) colored root tips with a touch of reddish-purple (RHS N77C).

Plant:

*Commercial crop time to flowering*.—Following asexual propagation (in-vitro), the rooted cuttings grow for 20-24 weeks. After transplantation into 12-cm pots, the plants are finished after 48 to 50 weeks.

*Growth habit of the peduncle*.—Upright to slightly pendant with raceme inflorescence.

*Height (from soil level to top of inflorescence)*.—Approximately 55.0 cm to 60.0 cm.

*Width (measured from leaf tips)*.—About 37.0 cm to 39.0 cm.

*Vigor*.—Strong.

Leaves:

*Mature leaves*.—Quantity per plant: 8 to 10 leaves are produced before flowering. Length (fully expanded): 21.0 cm to 23.0 cm. Width: 7.0 cm to 8.0 cm. Position of the broadest part of the leaf: Toward the apex. Shape: Obovate. Base shape: Moderately elongated. Apex: Obtuse unequal. Leaf blade angle with the petiole (measured from the horizontal position): Between 20 degrees and 45 degrees. Leaf margin: Entire. Color: Upper surface: RHS 146A. Lower surface: RHS 146B with reddish-brown edge (RHS 200B). Texture (both upper and lower surfaces): Smooth. Thickness: 2.0 mm to 3.0 mm. Variegation: Absent. Venation: Pattern: Parallel. Color of the midvein: Upper surface: RHS 146A. Lower surface: RHS 146B with a hint of brown (RHS 200C).

Peduncle:

*Quantity per plant*.—1 to 2.

*Number of flowers per peduncle*.—12 to 15.

*Length*.—55.0 cm to 60.0 cm.

*Diameter*.—6.0 mm to 7.0 mm.

*Strength*.—Strong.

*Aspect*.—Upright to slightly pendant.

*Texture*.—Smooth.

*Color*.—Mix of brown (RHS 200B) and green (RHS 146C).

*Internode length*.—4.0 cm to 5.0 cm.

Inflorescence description:

*Appearance*.—Upright to slightly pendant, raceme inflorescence with bilaterally symmetrical flowers that open in succession beginning with the lowermost flower.

*Number of inflorescences*.—1 to 2.

*Inflorescence size*.—Height (from base to tip): 260.0 mm to 280.0 mm.

*Flowering time*.—First flowers can be expected 10 to 11 months after planting in a 12-cm pot.

*Flower*.—Height: 75.0 mm to 80.0 mm. Diameter: 92.0 mm to 97.0 mm. Depth of lip: 24.0 mm to 26.0 mm.

*Flower longevity*.—On the plant: 10 to 13 weeks.

*Flower shape*.—Flat.

*Fragrance*.—Absent.

*Flower bud*.—Average size: Medium to large. Length: 24.0 mm to 26.0 mm. Width: 19.0 mm to 21.0 mm. Shape: Egg shaped. Color: Mix of RHS N77B and 146C.

*Petals*.—Arrangement: Open/free. Shape: Semi-circular. Apex: Rounded to emarginated asymmetric. Margin: Entire. Length (from base to tip): 44.0 mm to 46.0 mm. Width: 58.0 mm to 60.0 mm. Position of the broadest part of the petal: Toward the base. Color (when fully opened): Upper surface: Basic color: Light purple (RHS 76A). Over color: Very light purple (RHS 76B) at the base; purplish-pink shade (RHS N78C); small white edge (RHS NN155C). Lower surface: Basic color: Light purple (RHS 76A). Over color: Light reddish-purple (RHS N78D) at the base and purplish-pink stripes (RHS N78C); small white edge (RHS NN155C). Number of spots and stripes on the petals (upper surface): Many. Color of spots and stripes on the petals (upper surface): RHS N78B. Density of netting of the petals (upper surface): None. Color of the netting (upper surface): None.

*Dorsal sepal*.—Shape: Elliptic. Apex: Slightly emarginated symmetric. Margin: Entire. Length (from base to tip): 44.0 mm to 46.0 mm. Width: 32.0 mm to 34.0 mm. Position of the broadest part of the dorsal sepals: In the middle. Color (when fully opened): Upper surface: Basic color: Light purple (RHS 76A). Over color: Purplish-pink (RHS N78C). Lower surface: Basic color: Light reddish-purple (RHS N78D). Over color: Greyish yellow-green (RHS 195B). Number of spots and stripes on the dorsal sepals (upper surface): Medium to many. Color of spots and stripes on the dorsal sepals (upper surface): RHS N78C. Density of netting of the dorsal sepals (upper surface): Low at the edge. Color of the netting (upper surface): Purplish-pink (RHS N78C).

*Lateral sepals*.—Shape: Ovate. Apex: Obtuse symmetric. Margin: Entire. Length (from base to tip): 45.0 mm to 47.0 mm. Width: 26.0 mm to 28.0 mm. Position of the broadest part of the lateral sepals: At the base. Color (when fully opened): Upper surface: Basic color: Light purple (RHS 76A). Over color: Slightly light yellow-green (RHS 145C). Lower surface: Basic color: Light reddish-purple (RHS N78D). Over color: Light yellow-green (RHS 145C) in the middle with reddish-purple midvein (RHS N78B) toward the tip. Number of spots and stripes on the lateral sepals (upper surface): At the base spots: medium and stripes: medium. Color of spots and stripes on the lateral sepals (upper surface): Spots (RHS 184B) and stripes (RHS N78B). Density of netting of the lateral sepals (upper surface): None. Color of the netting (upper surface): None.

*Labellum* (*lip*).—Whiskers: Present. Length of whiskers: 11.0 mm to 13.0 mm. Color of whiskers: Dark purplish-red (RHS N79C) with dark red tips (RHS 187B). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Entire. Length: 20.0 mm to 22.0 mm. Width: 15.0 mm to 17.0 mm. Color: Upper surface: White (RHS NN155D) with a touch of yellow (RHS 8A) at the base; dark red (RHS 187C) on one side and reddish-purple (RHS N78A) toward the other side. Lower surface: Yellowish-white (RHS 156D) at the base with a touch of purplish-pink (RHS N78C); dark red (RHS 187C) on one side and reddish-purple (RHS N78A) toward the other side. Number of spots and stripes on the lateral lobe: Few stripes at the base. Color of spots and stripes on the lateral lobe: RHS 185A. Density of netting of the lateral lobe: None. Color of the netting: None.

*Apical lobe*.—Shape: Triangular. Margin: Entire. Length: 23.0 mm to 25.0 mm. Width: 21.0 mm to 23.0 mm. Color: Upper surface: Red (RHS 185A to 185B) at the base and wings and reddish-purple (between RHS N78A and NN78A) toward the whiskers. Lower surface: Touch of light yellow-green (RHS 195C) at the base; red wings (RHS 185A); light purple (RHS 76A) in the middle and reddish-purple (between RHS N78A and NN78A) toward the margin. Number of spots and stripes on the apical lobe (upper surface): None. Color of spots and stripes on the apical lobe (upper surface): None. Density of netting of the apical lobe (upper surface): None. Color of the netting (upper surface): None.

*Callus*.—Average size: Medium. Height: 6.0 mm to 7.0 mm. Length: 5.0 mm to 6.0 mm. Width: 4.0 mm to 5.0 mm. Color: Yellow (RHS 7A) with red spots (RHS 178A).

Reproductive organs:

*Column*.—Length: 7.0 mm to 9.0 mm. Diameter: 5.0 mm to 6.0 mm. Color: Reddish-purple (RHS N78A).

*Pollinia*.—Quantity: 2. Diameter: 0.9 mm to 1.2 mm. Color: Orange (RHS 24A).

*Ovary*.—Length: 10.0 mm to 12.0 mm. Diameter: 2.0 mm to 3.0 mm.

*Pedicel*.—Length: 34.0 mm to 36.0 mm. Diameter: 2.0 mm to 3.0 mm. Texture: Smooth. Color: Purplish-red (RHS N77B) at the base; yellow-green (RHS 195B) and purplish-pink (RHS 186D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGUIQDI' differs from female parent plant '23426-01' (unpatented) in that 'PHALGUIQDI' has reddish-purple (RHS N78A) columns and dark purplish-red (RHS N79C) whiskers with dark red tips (RHS 187B), whereas '23426-01' has light purple (RHS 76A) columns at the base with reddish-purple (RHS N78B) toward the tips and reddish-purple (RHS N78B) whiskers with yellow tips. Additionally, 'PHALGUIQDI' has shorter whiskers than '23426-01'.

'PHALGUIQDI' differs from male parent plant '14261-01' (unpatented) in that 'PHALGUIQDI' has dark purplish-red (RHS N79C) whiskers with dark red tips (RHS 187B), whereas ,'14261-01' has red-purple (RHS 71A) whiskers. Additionally, 'PHALGUIQDI' has shorter whiskers than '14261-01'.

'PHALGUIQDI' is most similar to the commercial *Phalaenopsis* plants named 'PHALDESBIM' (U.S. Plant Pat. No. 27,671) and 'PHALOFMO' (U.S. Plant Pat. No. 28,736). 'PHALGUIQDI' differs from the commercial variety 'PHALDESBIM' in that 'PHALGUIQDI' has larger flowers than 'PHALDESBIM'.

'PHALGUIQDI' differs from the commercial variety 'PHALOFMO' in that 'PHALGUIQDI' has reddish-purple (RHS N78A) columns, whereas 'PHALOFMO' has columns that are RHS 76B at the base and RHS N78B toward the tips. Additionally, 'PHALGUIQDI' has smaller flowers than 'PHALOFMO'.

I claim:

1. A new and distinct variety of *Phalaenopsis* plant named 'PHALGUIQDI', substantially as described and illustrated herein.

* * * * *